(12) United States Patent
Root et al.

(10) Patent No.: US 7,981,091 B2
(45) Date of Patent: Jul. 19, 2011

(54) SMALL DIAMETER INTRAVASCULAR CATHETER WITH SCREW TIP AND LIMITED TORSIONAL DISPLACEMENT

(75) Inventors: Howard Root, Excelsior, MN (US); Jeff Welch, Maple Grove, MN (US); Jason Garrity, Minneapolis, MN (US); Dean Peterson, Rogers, MN (US)

(73) Assignee: Vascular Solutions, Inc., Minneapolis, MN (US)

( * ) Notice: Subject to any disclaimer, the term of this patent is extended or adjusted under 35 U.S.C. 154(b) by 941 days.

(21) Appl. No.: 11/585,371

(22) Filed: Oct. 24, 2006

(65) Prior Publication Data

US 2008/0172008 A1      Jul. 17, 2008

(51) Int. Cl.
*A61M 5/00* (2006.01)
*A61M 25/00* (2006.01)

(52) U.S. Cl. ........................ 604/264; 604/523
(58) Field of Classification Search .................. 604/264, 604/523–532
See application file for complete search history.

(56) References Cited

U.S. PATENT DOCUMENTS

| | | | |
|---|---|---|---|
| 5,078,723 A | | 1/1992 | Dance et al. |
| 5,415,634 A | * | 5/1995 | Glynn et al. ............. 604/103.08 |
| 5,423,846 A | | 6/1995 | Fischell |
| 5,658,264 A | * | 8/1997 | Samson ......................... 604/526 |
| 5,741,429 A | | 4/1998 | Donadio, III et al. |
| 5,968,064 A | | 10/1999 | Selmon et al. |
| 6,511,462 B1 | | 1/2003 | Itou et al. |
| 6,666,874 B2 | | 12/2003 | Heitzmann et al. |
| 6,921,397 B2 | | 7/2005 | Corcoran et al. |

OTHER PUBLICATIONS

Website: http://abbottvasculardevices.com/products/product.php; Abbott Vascular Devices; ASAHI—TORNUS; (12 pages), Apr. 26, 2006.
Website: http://bostonscientific.com/med_specialty/deviceDetail; Flextome™ Cutting Balloon® Dilatation Device; (6 pages), Apr. 26, 2006.
Website: www.angioscore.com/products/; AngioSculpt Scoring Balloon Catheter—The Evolution of Angioplasty; (3 pages), Apr. 26, 2006.

* cited by examiner

*Primary Examiner* — Kevin C Sirmons
*Assistant Examiner* — Imani Hayman
(74) *Attorney, Agent, or Firm* — Patterson Thuente Christensen Pedersen, PA

(57) ABSTRACT

A catheter to be passed over a guidewire, including a screw portion with a cylindrical hollow shaft and a helical thread portion extending outwardly from the hollow shaft. The screw portion is secured coaxially to a tubular portion formed from a substantially rigid material. The tubular portion has, along a portion of its length, at least two slits having a pattern geometry that limits torsional displacement. The catheter also includes a hub having a lumen joined substantially coaxially to the tubular portion.

22 Claims, 6 Drawing Sheets

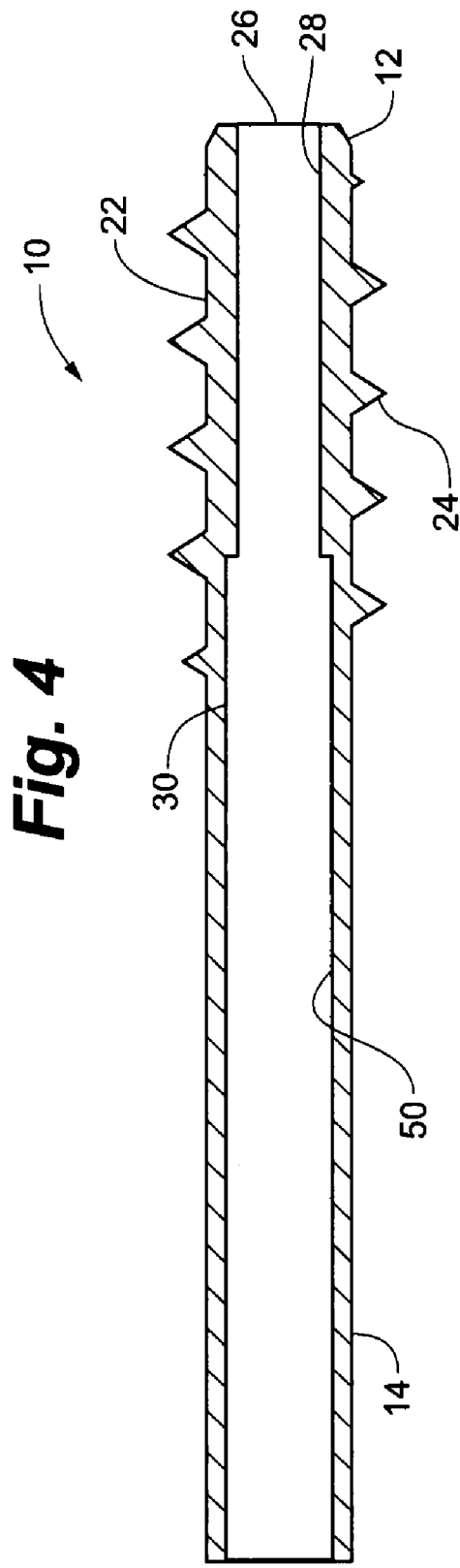

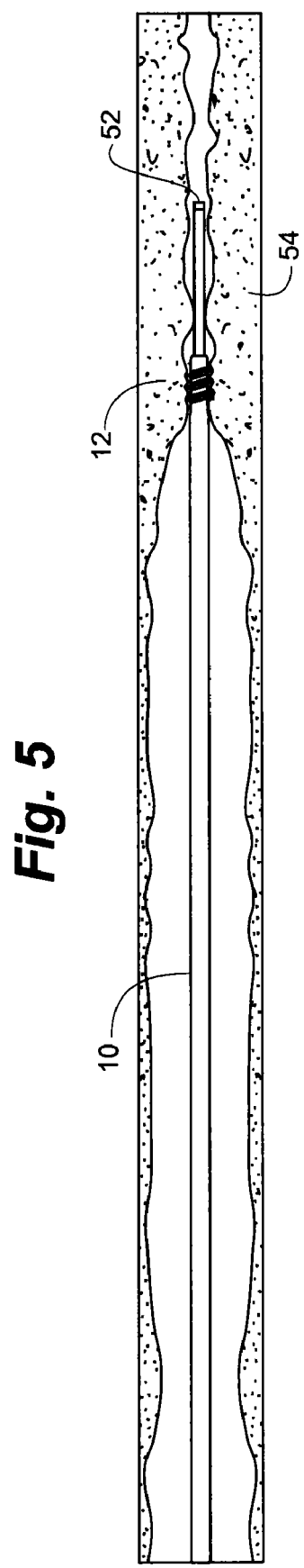

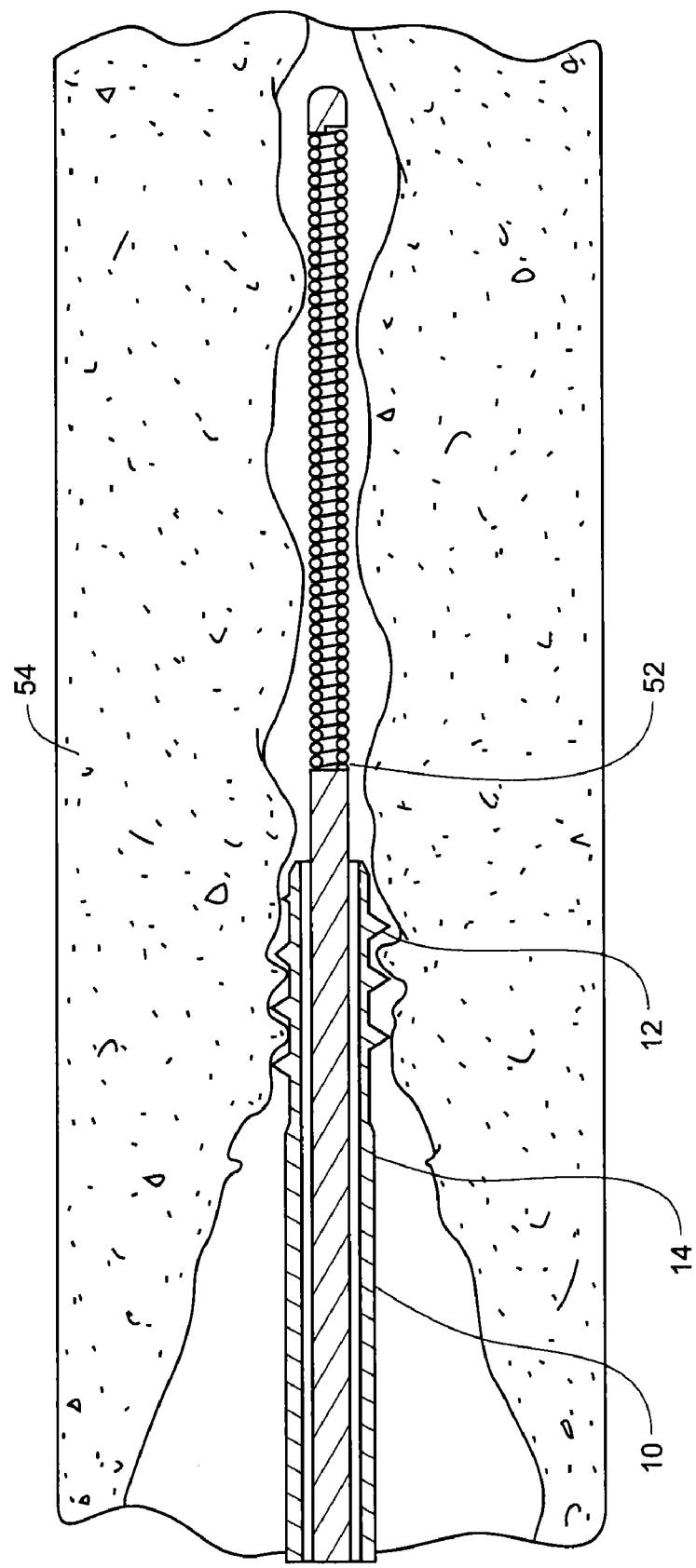

SMALL DIAMETER INTRAVASCULAR CATHETER WITH SCREW TIP AND LIMITED TORSIONAL DISPLACEMENT

FIELD OF THE INVENTION

The invention relates generally to the field of interventional cardiology devices. More particularly, the invention relates to interventional cardiology devices to assist in passing a stent or balloon through a vascular stenosis.

BACKGROUND OF THE INVENTION

There are many situations in which an interventional cardiologist needs to pass an interventional cardiology device, such as a stent or balloon, beyond a narrowing vascular lesion, or vascular stenosis. Often, it is found that it is possible to pass a guidewire through a stenotic or blocked artery but that the stenosis or blockage prevents the passage of a larger device, such as a balloon or stent carried by an intravascular catheter.

Previous approaches to this problem have often involved attempts to increase the size of the available lumen. This approach generally involves auger-like cardiology devices that seek to drill or abrade their way through a stenotic lesion. This approach is sometimes referred to as debulking the lesion. Examples of such devices are found in U.S. Pat. Nos. 5,078,723, 5,968,064 and 6,666,874. Auger like devices tend to dislodge pieces of atherosclerotic plaques. The dislodged pieces can be released into the blood circulation and create emboli that may create circulatory blockages downstream from the location of the initial stenosis.

Torsional displacement is one of the problems encountered with previous approaches that can happen when applying torque or torsional forces to intravascular catheters. Small diameter intravascular catheters are typically less than two millimeters in diameter and must be flexible to navigate the tortuous paths taken by blood vessels within the body. Materials that allow the desired flexibility tend to not transmit torque forces as well as is desired. That is, the application of torque to a catheter would ideally lead to rotation of the entire catheter about its long axis; however, intravascular catheters made of flexible materials tend to deform under torque loads instead of transmitting the torque force consistently along their length. Depending on the amount of torque applied smoothly at one end of a catheter that torsional force may be transmitted unevenly at the opposing end of the catheter. Thus, a smooth turning at one end may lead to a jerky rotational motion at the other end as torque force is alternately transmitted and stored by torsional displacement of the catheter tube. In a severe case, this may lead to kinking of the tubular portion of the catheter.

It would be desirable to have a catheter that could transmit torque forces evenly along the longitudinal axis of the catheter and with minimal torsional displacement of the catheter while still having enough flexibility to navigate tortuous blood vessels.

It would also be desirable to provide a device that would permit the passage of interventional cardiology devices larger than a guidewire beyond stenotic lesions without dislodging emboli that may create other complications.

SUMMARY OF THE INVENTION

In one embodiment, the present invention includes a small diameter intravascular catheter made of metal or another rigid material that includes a threaded tip with threads protruding outwardly that exceed the diameter of the catheter tube. The threaded portion of the catheter of the present invention is utilized to engage and pull through the lesion rather than to auger or abrade out material in the lesion. The catheter of one embodiment of the present invention also includes a wall pierced by slits that wind helically around the catheter. In one embodiment of the invention, the slits have a pattern geometry that limits torsional displacement and may include areas of sigmoid curves periodically spaced along the longitudinal length of the slit portion of the catheter having the slits.

The catheter of the present invention may also include an inner polyimide or Teflon liner. In addition, the catheter of the present invention may include an external polyurethane coating. In one embodiment the catheter of the present invention may also include a hub of a luer lock type. In one aspect of this embodiment, a strain relief may be provided such as by a heat shrink tubing at the juncture between the hub and the catheter.

The present invention may also include a torque device which can be fastened to the catheter in order to provide for application of torque to the catheter and thus to the screw. The screw portion of the catheter of one embodiment the present invention defines an interior lumen which is contiguous with lumen of the tubular structure.

The intravascular catheter of one embodiment of the present invention has enhanced flexibility in the distal-most 20-40 centimeters provided by laser cutting of a pattern geometry in the tubular material of the catheter. The catheter may be formed from a metallic hypotube. The hypotube may be formed, for example from Nitinol or stainless steel. The pattern geometry allows flexibility by using a helical pattern but also provides a pattern geometry that limits torsional displacement when torque is applied to the tubular portion of the catheter.

In another aspect of the invention, the tip of the catheter has a helical thread pattern which is larger in diameter than the tubular portion. For example, the threaded portion of the tip of the catheter may be about 1.5 times larger in diameter as measured at the outside of the threaded portion.

As the catheter of the present invention is passed through a stenotic lesion it creates a plastic deformation of the lesion with scoring lines created by passage of the screw threads. It is notable that the lesion is not broken up, debulked or drilled out but deformed toward the walls of the blood vessel.

For the purposes of this application, intravascular catheters are generally considered to be those having a diameter less than or equal to about twelve French. More likely they have a diameter less than six French. Small diameter intravascular catheters are those having a diameter of about three French or less.

The application of torque or torsional forces to the catheter varies between when the catheter is being manipulated through the vasculature and when the screw portion of the catheter is brought into contact with a lesion. When the catheter is being passed through the often tortuous vasculature there is minimal resistive torque encountered overall and particularly little resistive torque that arises from the screw tip. Resistive torque arises primarily from incidental contact between the catheter and the walls of the blood vessel.

When the screw tip portion is brought into contact with the lesion and the screw tip is being advance through the lesion resistive torque arises in large measure from the lesion resisting passage of the screw tip portion as the material of the stenotic lesion is plastically deformed and displaced by passage of the screw tip.

Once the stenotic lesion has been plastically deformed the resistive torque that is encountered in removing the screw tip from the lesion by reversing the rotation of the catheter is considerably less than that required to advance the screw tip through the lesion. Thus, the pattern geometry of the slits in the tubular portion is such that it is preferably biased to being more resistant to torsional displacement when the screw tip is being advanced through the lesion than when the screw tip is being withdrawn from the lesion.

BRIEF DESCRIPTION OF THE DRAWINGS

FIG. 4 is a cross-sectional view taken along section line 4-4 of FIG. 3.

FIG. 5 is a schematic sectional view of a catheter in accordance with the present invention in situ in blood vessel that has a stenotic lesion.

FIG. 6 is a detailed schematic sectional view of a catheter in accordance with the present invention in situ in blood vessel that has a stenotic lesion.

DETAILED DESCRIPTION OF THE DRAWINGS

Figure 1:
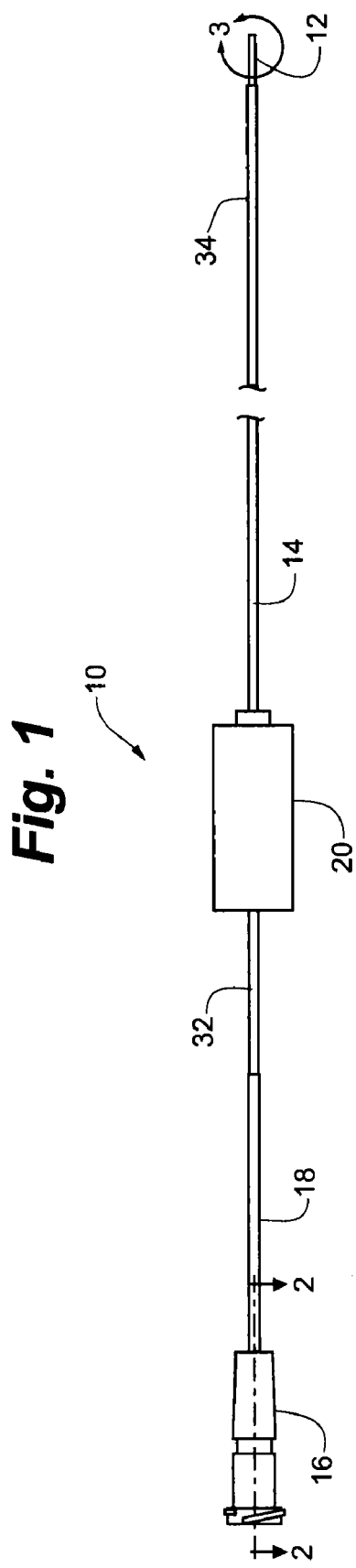
FIG. 1 is a plan view of a catheter in accordance with the present invention.
Figure 2:
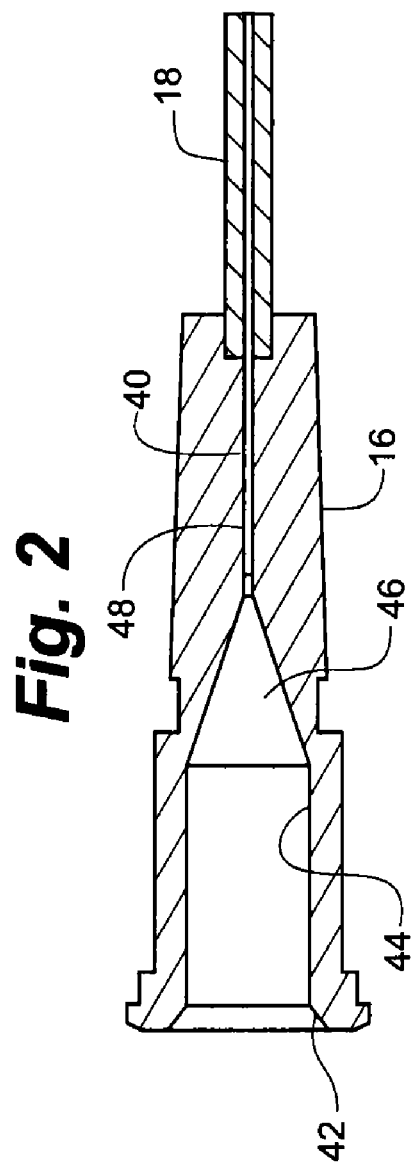
FIG. 2 is a sectional view of a hub joined to a tube portion taken along section line 2-2 of FIG. 1.

Catheter 10, of one embodiment of the present invention, generally includes screw portion 12, tube portion 14, hub 16, strain relief 18, and torque device 20. Referring to FIG. 1, in one aspect of the invention, screw portion 12 is located distally followed by tube portion 14 and hub 16 located proximally. Strain relief 18 may be located generally at the juncture of tube portion 14 and hub 16. In one embodiment of the invention, torque device 20 may be located along the length of tube portion 14 or at hub 16.

Figure 3:
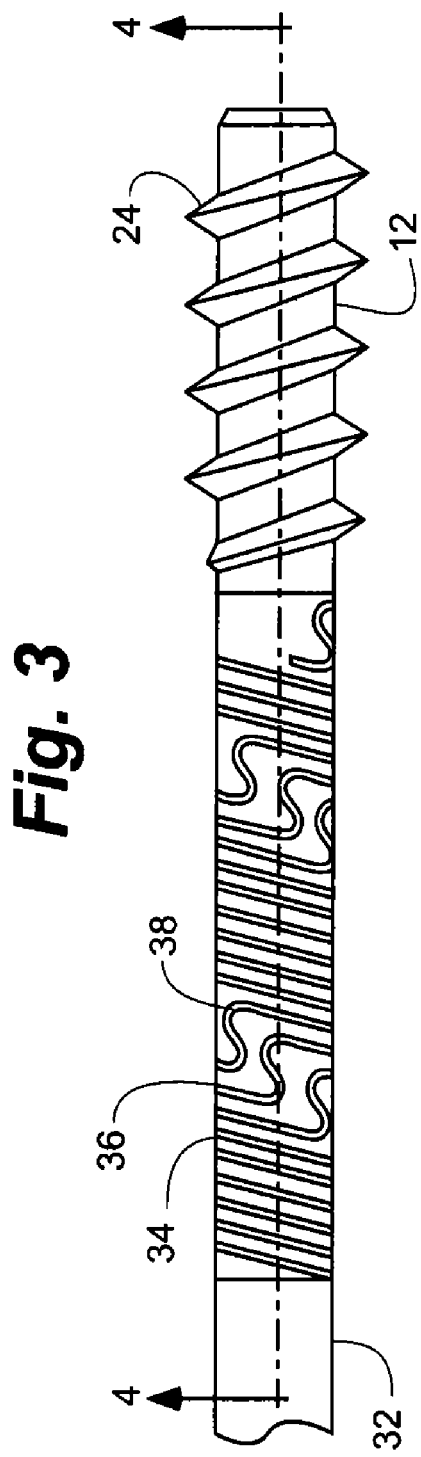
FIG. 3 is a detail plan view of a screw tip and part of a tube portion taken from FIG. 1.

Referring particularly to FIGS. 3 and 4, depicting an embodiment of the invention, screw portion 12 generally includes hollow shaft 22 and helical thread 24. Screw portion 12 may be formed from a rigid biocompatible material, for example, 304 stainless steel. Screw portion 12 may be gold plated or coated with another biologically inert material or formed entirely from a biocompatible material. Hollow shaft 22 defines screw lumen 26. Hollow shaft 22 defines smaller diameter portion 28 of screw lumen 26 and larger diameter portion 30 of screw lumen 26. Hollow shaft 22 may have an outside diameter, for example, of about two French or approximately 0.66 millimeters. It is notable that helical thread 24 extends outwardly from hollow shaft 22 and has an outer diameter somewhat larger than hollow shaft 22. Hollow shaft 22 is of a similar diameter as tube portion 14 and, in one aspect of the invention is generally cylindrical. For example, helical thread 24 of the tip of the catheter 10 may be about 1.5 times larger in diameter as measured at the outside of the helical thread 24. For example, helical thread 24 may have a diameter of about three French, approximately one and one half times the diameter of hollow shaft 22. The diameter of hollow shaft 22 may be substantially equal to the diameter of tube portion 14, which may be about two French.

Tube portion 14 may be formed from a rigid biocompatible material. In one aspect of the invention, tube portion 14 may be formed from metal. In another aspect of the invention, tube portion 14 may be formed from 304 stainless steel hypotube having an outside diameter of approximately two French. Titanium or other known metallic materials may also be used.

In one aspect of the invention, tube portion 14 includes solid portion 32 and helically cut portion 34. In one embodiment of the invention, helically cut portion 34 extends along approximately the distal twenty five centimeters of tube portion 14 ending shortly before the junction of tube portion 14 with screw portion 12. Helically cut portion 34 may be formed, for example, by laser cutting. Helically cut portion 34 may also be formed by other techniques known to the art such as etching or machining. Helically cut portion 34 may include, for example, four helices 36.

Each of helices 36 may include sigmoid curve 38. Sigmoid curves 38 may repeat along the length of tube portion 14 with a generally regular periodicity or an irregular periodicity. Tube portion 14 may be joined to screw portion 14 by the use of laser welding techniques or adhesive techniques, for example.

In one aspect of the invention, hub 16 is located at the proximal end of catheter 10. Hub 16 may be, for example, a standard female luer adapter. Hub 16 may be formed of metal or a polymer material. Hub 16 is fixedly joined to solid portion 32 of tube portion 14. Hub 16 defines hub lumen 40 inside thereof. Hub lumen 40 may include entry taper 42, large lumen portion 44, tapered funnel 46, and small lumen portion 48. Small lumen portion 48 has an inside diameter similar to that of tube portion 14 and hollow shaft 22.

The interior of tube portion 14, as well as small lumen portion 48 of hub 16 and larger diameter portion 30 of screw portion 12, may be lined by liner 50. Liner 50 may be formed of polyimide and Teflon, in one embodiment of the invention. Other liner materials may be used as well. The exterior of tube portion 14 may be coated with a polymer coating such as polyurethane.

Strain relief 18 may cover the proximal portion of tube portion 14. Strain relief 18 may be formed of a heat shrink wrap tubing.

Referring again to FIG. 1, in one aspect of the invention, torque device 20 may be removably attachable or permanently attached to tube portion 14. Torque device 20 is dimensioned to allow easy hand gripping by a physician using catheter 10. Torque device 20 may be adjustable and positioned along the length of tube portion 14. Torque device 20 may also be secured to hub 16.

Referring to FIGS. 5 and 6, catheter 10 is intended to be inserted over guidewire 52 after guidewire 52 has been passed at least partially through a lesion in the vasculature. FIGS. 5 and 6 depict guidewire 52 partially inserted through stenotic lesion 54. Guidewire 52 is inserted into lesion prior to placement of catheter 10. Guidewire 52 may be inserted partially or completely through stenotic lesion 54 before catheter is inserted over guidewire 52.

In operation, catheter 10 is inserted into a large blood vessel over a preplaced guidewire 52 which has been passed at least partially through a stenosis. When catheter 10 is inserted over the guidewire 52, the guidewire 52 has already been passed through a stenosis or blockage in a blood vessel. Screw portion 12 is brought into abutment with stenotic lesion 54 pierced or transited by guidewire 52. An operator of catheter then grasps torque device 20 and turns catheter 10 by turning torque device 20.

Torque device 20 transfers rotational motion to solid portion 32 of tube portion 14. The turning of solid portion 32 applies torque to helically cut portion 34. The presence of sigmoid curves 38 locks helices 36 such that torque may be applied to screw portion 14 where it abuts the stenotic lesion 54. Helices 36 lock helically cut portion 34 such that helically cut portion 34 can transmit torque forces without excessive "winding up" helically cut portion 34.

Referring to FIGS. 5 and 6, helical thread 24 engages to the stenotic lesion 54. The engagement of helical thread 24 with lesion 54 forces the opening made by the guidewire in lesion 54 to expand by plastic deformation and displacement of lesion 54 material. It is notable that helical thread 24 does not auger, abrade or otherwise remove material from lesion 54. Screw portion 12 plastically deforms the material of lesion 54 to displace it and to create a larger passageway for an interventional cardiology device to pass through without removing material from lesion 54. In addition, catheter 10 is drawn forward through lesion 54 taking along with it any interventional cardiology device attached thereto.

As it passes through stenotic lesion 54, helical thread 24 scores interior surfaces of stenotic lesion 54 creating a smoother lumen therethrough than previously existed. In addition, helical thread 24 leaves a scored impression on the walls of lesion 54. This may have the beneficial effect of reducing turbulence within the narrowed lumen created by stenotic lesion 54 by improving laminar flow along the lumen walls thus decreasing the risk of embolus formation at lesion 54.

The foregoing description of an exemplary embodiment of the invention has been presented for the purpose of illustration and description. It is not intended to be exhaustive or to limit the invention to the precise form disclosed. Many modifications and variations are possible in light of the above teaching. It is intended that the scope of the invention not be limited with this detailed description, but rather by the claims appended hereto.

The invention claimed is:

1. An intravascular catheter to be passed over a guidewire, the catheter comprising:
   a rigid screw portion comprising a rigid hollow cylindrical shaft having a substantially constant diameter, the rigid hollow shaft defining a cylindrical lumen longitudinally therethrough and said screw portion having a rigid helical thread portion extending outwardly from an outer surface of the hollow shaft; and
   a tubular portion formed from a substantially rigid material, having a length, joined substantially coaxially to the screw portion and defining a lumen that is continuous with the lumen of the screw portion, the tubular portion including at least two slits defined along at least some of the tubular portion, the two slits having a pattern geometry that limits torsional displacement of at least a portion of the catheter, the at least two slits having a first end and a second end, the first end and the second end being longitudinally displaced from one another along the length of the tubular portion, wherein the lumen of the screw portion and the lumen of the tubular portion are dimensioned to pass over a guidewire.

2. The catheter as claimed in claim 1,
   in which the tubular portion has a first diameter and the hollow shaft of the screw portion has a second diameter and the first and second diameter are substantially equal;
   the helical thread portion has a first handedness and the slits are generally helical and have a second handedness opposed to the first handedness;
   the slits are generally helical and the generally helical slits further include sigmoid curves that repeat along the length of the tubular portion with a substantially regular periodicity;
   the tubular portion has a diameter of about two French and further comprising an inner liner and an outer coating; and
   a hub having a lumen joined substantially coaxially to the tubular portion.

3. The catheter as claimed in claim 1, in which the helical thread portion has an outside diameter significantly larger than the second diameter of the hollow shaft.

4. The catheter as claimed in claim 3, in which the first diameter of the helical thread portion is at least about one and one third times the second diameter of the hollow shaft.

5. The catheter as claimed in claim 1, further comprising a torque device couplable to the tubular portion whereby torque can be applied to the tubular portion.

6. The catheter as claimed in claim 1, in which the pattern geometry is such that torsional displacement is limited to a greater degree in a first rotational direction than in a second rotational direction.

7. A method of controlling flexibility and torsional displacement in an intravascular catheter, comprising:
   forming a portion of the catheter from a unitary tubular substantially rigid structure having a wall and a length and defining a lumen;
   piercing the wall with at least two continuous slits along a substantial portion of the length of the wall, each slit having a first end and a second end, the first end and the second end being longitudinally displaced from each other along the length of the tubular substantially rigid structure thereby imparting flexibility to the tubular substantially rigid structure; and
   forming the slits with a pattern geometry that limits torsional displacement of at least a portion of the catheter.

8. The method as claimed in claim 7, further comprising forming a helical thread portion at a distal end of the catheter that has a first handedness and forming the slits such that they are generally helical and have a second handedness opposed to the first handedness.

9. The method as claimed in claim 7, further comprising forming the helical thread portion to have right handed pitch the slits have left handed pitch.

10. The method as claimed in claim 7, further comprising forming the generally helical slits to further include sigmoid curves.

11. The method as claimed in claim 10, further comprising forming the sigmoid curves to repeat along the length of the tubular portion with a substantially regular periodicity.

12. The method as claimed in claim 7, further comprising constructing the pattern geometry such that torsional displacement is limited to a greater degree in a first rotational direction than in a second rotational direction.

13. The method as claimed in claim 7, further comprising:
   forming a helical thread portion at a distal end of the catheter that has a first handedness and forming the slits such that they are generally helical and have a second handedness opposed to the first handedness;
   forming the generally helical slits to further include sigmoid curves;
   forming the sigmoid curves to repeat along the length of the tubular portion with a substantially regular periodicity; and
   constructing the pattern geometry such that torsional displacement is limited to a greater degree in a first rotational direction than in a second rotational direction.

14. An intravascular catheter to be passed over a guidewire, the catheter comprising:
   a rigid screw portion comprising a rigid hollow cylindrical shaft having a substantially constant first diameter, the rigid shaft defining a hollow cylindrical lumen and said screw portion having a helical thread portion extending outwardly from an outer surface of the hollow shaft;
   a tubular portion formed at least in part from a substantially rigid material, having a length, joined substantially coaxially to the screw portion and defining a lumen that is continuous with the lumen of the screw portion, the tubular portion having a second diameter substantially equal to the hollow shaft first diameter; and a hub having a lumen joined substantially coaxially to the tubular portion.

15. The catheter as claimed in claim 14, in which the tubular portion defines along a portion of its length at least two slits having a pattern geometry that limits torsional displacement of at least a portion of the catheter, the at least two slits having a first end and a second end, the first end and the second end being longitudinally displaced from each other along the length of the tubular substantially rigid structure.

16. The catheter as claimed in claim 15, in which the helical thread portion has an outside diameter significantly larger than the first diameter of the hollow shaft.

17. The catheter as claimed in claim 14, in which an outside diameter of the helical thread portion is at least about one and one third times the diameter of the first diameter of the hollow shaft.

18. The catheter as claimed in claim 15, in which the helical thread portion has a first handedness and the slits are generally helical and have a second handedness opposed to the first handedness.

19. The catheter as claimed in claim 18, in which the generally helical slits further include sigmoid curves that repeat along the length of the tubular portion with a substantially regular periodicity; and further comprising a torque device couplable to the tubular portion whereby torque can be applied to the tubular portion; and an inner liner and an outer coating.

20. The catheter as claimed in claim 14, in which the tubular portion has a diameter of about two French.

21. The catheter as claimed in claim 15, in which the pattern geometry is such that torsional displacement is limited to a greater degree in a first rotational direction than in a second rotational direction.

22. An intravascular catheter to be passed over a guidewire, comprising:

a screw portion comprising a hollow cylindrical shaft having a substantially constant first diameter, the shaft defining a hollow cylindrical lumen and said screw portion having a helical thread portion extending outwardly from an outer surface of the hollow shaft;

a tubular portion formed from a substantially rigid material, having a length, joined substantially coaxially to the screw portion and defining a lumen that is continuous with the lumen of the screw portion, the tubular portion having a second diameter substantially equal to the hollow shaft first diameter; and a hub having a lumen joined substantially coaxially to the tubular portion;

in which the tubular portion defines along a portion of its length at least two slits having a pattern geometry that limits torsional displacement, the at least two slits having a first end and a second end, the first end and the second end being longitudinally displaced from each other along the length of the tubular portion;

in which the helical thread portion has an outside diameter significantly larger than the first diameter of the hollow shaft;

in which the helical thread portion has a first handedness and the slits are generally helical and have a second handedness opposed to the first handedness;

in which the generally helical slits further include sigmoid curves that repeat along the length of the tubular portion with a substantially regular periodicity;

in which the pattern geometry is such that torsional displacement is limited to a greater degree in a first rotational direction than in a second rotational direction;

in which the pattern geometry is such that torsional displacement is limited to a greater degree in a first rotational direction than in a second rotational direction; and further comprising a torque device couplable to the tubular portion whereby torque can be applied to the tubular portion; and an inner liner and an outer coating.

* * * * *

UNITED STATES PATENT AND TRADEMARK OFFICE
CERTIFICATE OF CORRECTION

| | | |
|---|---|---|
| PATENT NO. | : 7,981,091 B2 | Page 1 of 1 |
| APPLICATION NO. | : 11/585371 | |
| DATED | : July 19, 2011 | |
| INVENTOR(S) | : Howard Root et al. | |

It is certified that error appears in the above-identified patent and that said Letters Patent is hereby corrected as shown below:

Col. 2, line 20 delete "one embodiment the present", and insert -- one embodiment of the present invention --

Col. 2, line 22, delete "contiguous with lumen of the", and insert -- contiguous with the lumen of the --

Col. 4, line 54, delete "An operator of catheter then", and insert -- An operator of catheter 10 then --

Col. 4, line 63, delete "without excessive "winding up" helically cut portion", and insert -- without excessively "winding up" helically cut portion --

Signed and Sealed this
Eighth Day of November, 2011

David J. Kappos
*Director of the United States Patent and Trademark Office*